United States Patent [19]
Pill et al.

[11] Patent Number: 5,192,806
[45] Date of Patent: Mar. 9, 1993

[54] METHOD OF PREVENTING PENILE TISSUE DEGENERATIVE CHANGE

[75] Inventors: Johannes Pill, Leimen; Johannes Aufenanger, Hirschberg; Thomas Konrad, Neckargemünd/Dilsberg; Klaus-Peter Jünemann, Mannheim, all of Fed. Rep. of Germany

[73] Assignee: Boehringer Mannheim GmbH, Fed. Rep. of Germany

[21] Appl. No.: 684,740

[22] Filed: Apr. 15, 1991

[30] Foreign Application Priority Data

Nov. 8, 1990 [DE] Fed. Rep. of Germany ..... 90121343
Dec. 22, 1990 [WO] PCT Int'l Appl. ... PCT/EP90/02299

[51] Int. Cl.$^5$ .......................................... A61K 31/195
[52] U.S. Cl. .................................. 514/562; 514/150; 514/573
[58] Field of Search ......................................... 514/562

[56] References Cited

PUBLICATIONS

Chemical Abstracts 109:22c (1988).
Chemical Abstracts 100:203371 (1984).

Primary Examiner—Leonard Schenkman
Attorney, Agent, or Firm—Nikaido, Marmelstein, Murray & Oram

[57] ABSTRACT

The present invention is concerned with the use of $TXA_2$ receptor antagonists for the preparation of pharmaceutical compositions for the prevention of degenerative changes in penile tissue.

12 Claims, No Drawings

METHOD OF PREVENTING PENILE TISSUE DEGENERATIVE CHANGE

The present invention is concerned with the preparation of pharmaceutical compositions for the prevention of degenerative changes in penile tissue.

Eicosanoids, such as prostaglandins, thromboxanes and leukotrienes, are a group of compounds present in the body which participate in physiological regulatory mechanisms. In this connection, these compounds are of importance for local regulation. They thereby act not only directly upon the reacting organ but also indirectly via other hormones and transmitter substances. Their especial importance appears to be a membrane-standing protective mechanism which, in the case of disturbance of the cellular integrity, is activated and, together with other factors, adapts the tissue to the stress situation. On the other hand, increased local concentrations of these compounds, for example in the case of tissue damage or destruction, can additionally contribute to an aggravation of the state of the disease (see K. Schrör, Prostaglandine, pub. Thieme-Verlag, Stuttgart, 1983; B. P. Curtis-Prior, Prostaglandins, pub. Churchill, Livingstone, Edinburgh, 1988). The particular pharmacological interest consists in that, by means of a selective intervention in these pathomechanisms, a damage of the organism in the widest sense or a disease can be prevented or treated.

In the case of erectile insufficiency, ultrastructural changes of the penile tissue have been found. As a characteristic pathological sign, there has been described a loss of the contractile myofilaments actin and myosin (see Diabetologica, 25, 424/1983). An aggregation of mitochondria is, in particular, to be ascertained in the early stage of this change (see Ophthalmologica, 191, 172/1985). In the case of the progress of these degenerative processes, further intracellular changes result, such as an increase of the perinuclear organelles, and cell nucleus degeneration (see Seminars in Urology, VIII (2), 80-93/1990). These pathological processes finally end in an atrophy of the corpus cavernosum (see Proceedings of the Third Biennial World Meeting on Impotence, Boston, Mass., Oct. 6-9, 1988). The morphological changes correlate with the clinical picture of erectile disturbances. It is obvious that the described degenerative changes and not the penile arteries play an important part in the pathology of the organically caused erectile disturbances (see Seminars in Urology, VIII (2), 80-93/1990). In a further investigation, a connection was discussed between a disturbed lipid metabolism and the vascular erectile dysfunction (see Int. J. Impotence Res., Sep., 2, 1990, Suupl. 2, 34).

Important changes in the case of the degeneration of the penile tissue, which cause an insufficiency of the erectile tissue of varying degree, are atrophy of the corpus cavernosum, cell nucleus degeneration and breakdown of the myofilaments. Active materials which prevent or greatly limit these processes are of therapeutic value in the case of a series of pathological conditions.

It is an object of the present invention to provide appropriate pharmaceutical compositions which can be used for the treatment of degenerative changes of the penile tissue.

In the scope of the present invention, we have now, surprisingly, found that $TXA_2$ receptor antagonists reduce degenerative changes in the penis which lead to an insufficiency of the erectile tissue.

Thus, the present invention is concerned with the use of $TXA_2$ receptor antagonists for the preparation of pharmaceutical compositions for the prevention of degenerative changes in penile tissue, including the prevention of atrophy of the corpus cavernosum, the prevention of the degeneration of cell nuclei and the prevention of the breakdown of myofilaments. Such degenerative processes can be caused physically, chemically, surgically or pathologically and include those caused by nicotine abuse and alcoholism.

Thromboxane (TX)-$A_2$ receptor antagonists are able to reduce degenerative changes in the tissue of the penis which arise in rabbits due to special diets. Therefore, the compounds are appropriate for the treatment and prevention of degenerative processes in the penile tissue which are to be detected in the case of the presence of risk factors, for example the taking of medicaments, nicotine abuse and alcoholism.

The $TXA_2$ receptor antagonists prevent the degeneration of the penile tissue in doses which are of the same order of magnitude as those which are usual in the case of the therapeutic use of $TXA_2$ receptor antagonists. It is to be expected that the suppression according to the present invention of degenerative processes in the penis and the prevention of insufficiency of the erectile tissue involved therewith by means of $TXA_2$ receptor antagonists will be of therapeutic value in the case of a series of clinical situations. Besides the above-mentioned risk groups, to these belong the prevention of a penis prothesis, as well as the prevention and/or reduction of the intravenous injection of papaverine, papaverine/phentolamine, prostaglandins and/or yohimbine.

$TXA_2$ receptor antagonists appropriate for the purpose of the present invention include sulotroban (BM 13.177), daltroban (BM 13.505), L-640,035, L-641,953, L-655,240, OKY-046, PKY-1581, ONO-1078, ONO-1270, ONO-3708, ONO-11113, SQ 28668, SQ 29548, SQ 30741, AH 23848, SK&F 88046, EP 045, S-145, Sch 37224, KF 4939, EG-626, N-benzyl-trimethoquinol analogues, 9,11-epoxy-9-homo-14-thiaprost-5-enoic acid derivatives, 13-azaprostanoic acid, 3-alkylaminopinane derivatives, pinane-$TXA_2$ derivatives, 9,11-azo-12-oxy-15-hydroxyprostanoic acid, 9,11-epoxy-iminoprosta-5,11-dienoic acid and dandrolen, all of which are mentioned in the Cumulate Index Medicus 1978-1989, subject index under Thromboxanes or Thromboxane-$A_2$ Antagonists and Inhibitors, as well as R 68070, AA 2414, SQ 33261, SQ 33552, FR 106881, BayU 3405, ICI 192695, L 670596, L 657925, L 657926, GR 32191, all of which are mentioned in Thrombosis and Haemostasis, 62 (1), 1-647/1989, and W-4099, SCRIP No.1537, 28/1990. As $TXA_2$ receptor antagonists, those compounds are especially preferred which are described in published European Patent Specifications Nos.0,031,954; 0,221,344; 0,223,593; 0,239,907; 0,304,271; 0,322,692; 0,325,245; 0,353,448; 0,356,989; 0,361,113 and 0,365,183, as well as in Federal Republic of Germany Patent Specification No. 40 06 640.1.

The investigations which can be regarded as being representative for all $TXA_2$ antagonists were carried out with daltroban (4-[2-(4-chlorophenyl) sulphonylaminoethyl]-phenylacetic acid). This compound is described in European Patent Specification No. 0,031,954. For the prevention of degenerative processes in the penile tissue, $TXA_2$ antagonists are administered systemically, preferably enterally and especially preferably orally but also parenterally (i.v.). The dosage varies according to the requirements of the individual patient and can be determined by the physician carrying out the treatment. For daltroban, in general, there should be administered a daily dosage of about 10 to 1000 mg. and especially of 100 to 800 mg. The dosage range of 100 to 800 mg. per day corresponds to that which is preferably employed therapeutically in the case of thromboxane-caused diseases. The daily dosage can be administered by a single administration or several times daily by the administration of appropriate partial amounts. The other TXA$_2$ receptor antagonists can be administered in agreement with the particular dosage instructions determined individually by the physician carrying out the treatment.

Because of the possibility of oral administration of the TXA$_2$ receptor antagonists, the period of treatment is not chronologically limited, which is of importance for the use according to the present invention.

As forms of administration for systemic administration, there can be used the conventional solid and liquid forms of administration, for example suppositories and solid oral forms of administration, such as capsules, tablets, lacquered tablets, dragees, pills, granulates and the like, or liquid forms of oral administration, such as solutions, syrups, suspensions, elixirs and the like, or parenteral forms of administration, such as infusion and injection solutions which can be injected intravenously or intramuscularly.

It lies within the scope of the present invention to incorporate the TXA$_2$ receptor antagonists into the enteral or oral forms of administration in any amount suitable for the administration. However, it is preferred to produce preparations which, per dosage unit, contain the active material in an amount of up to 800 mg. and preferably of about 100 or 200 mg. The production of capsules, tablets and lacquered tablets as dosage units is especially preferred. These can be administered one or more times daily, according to the particular requirements ascertained by the physician.

The production of the above-mentioned forms of use can take place in the conventional manner, for example as described in the following Example for daltroban.

EXAMPLE 1

Preparation of a Tabletting or Capsule Filling Mass

| Tablets containing 200 mg. daltroban: | |
|---|---|
| component | mg./capsule |
| 1. daltroban, fine | 200.0 |
| 2. lactose monohydrate | 50.0 |
| 3. crospovidon | 10.0 |
| 4. povidon 25,000 | 10.5 |
| 5. crospovidon | 5.0 |
| 6. colloidal silicon dioxide | 2.5 |
| 7. microcrystalline cellulose | 20.0 |
| 8. magnesium stearate | 5.0 |
| filling weight | 303.0 |

The components are mixed together in conventional manner and wet or dry granulated. The finished mass can be pressed to give cores and used directly as tablets or, coated with a film, can be used as film tablets. The mass can also be filled directly into capsules, for example into gelatine capsules of size 0.

EXAMPLE 2

Therapeutic Action

The therapeutic action of daltroban in the case of degenerative changes of the penile tissue can be seen from the following experiment.

a) General principle

The administration of special diets to rabbits results in a cell nucleus degeneration, an intracellular loss of the myofilament and an atrophy of the corpus cavernosum in the penis corresponding to the processes in the case of humans (see Investigative Urology, 3, 53–59/1989; Seminars in Urology, VIII (2), 80–93/1990). These processes lead to an insufficiency of the erectile tissue of varying degree. The diet was administered over the course of 96 days. In addition, daltroban was administered in a dosage of 10 mg./kg./day from the 42nd day. The study gives conclusions as to whether daltroban possesses an action on the degenerative processes in penile tissue. The chosen experimental design represents test conditions possibly made difficult with regard to the daltroban administration during the whole period of treatment but, having regard to a therapeutic use, comes closest to the situation in humans. The extent of the degenerative changes is subsequently determined from transversal sections of the penis on the basis of light and electronic microscopic expert evaluation.

b) Description of the experiment

Male white New Zealand rabbits with a body weight of about 2.0 kg. at the commencement of the experiment received, over the course of 96 days, a semi-synthetic diet consisting of casein, glucose/starch, cellulose and 0.5% cholesterol, as well as the conventional salt and vitamin mixtures. From the 42nd day, daltroban was additionally administered at a dosage of 10 mg./kg./day. The administration took place via the drinking water and was monitored via the consumption of water. At the end of the experiment, segments were taken from the apical, medial and basal part of the penis. For the morphological expert evaluation, the penis segments were fixed, dehydrated and finally embedded. The extent of the degenerative changes were determined with the help of light and transmission electronic microscopic expert evaluation on transverse sections of the penis segments. The following characteristics were used for the evaluation: myofilament breakdown, cell nucleus degeneration and atrophy of the corpus cavernosum.

c) Results

The animals additionally treated with daltroban from the 42nd day show, in the investigated penis segments, a distinctly smaller manifestation of the myofilament breakdown, of the cell nucleus degeneration and of the atrophy of the corpus cavernosum in comparison with the diet control animals. Rabbits fed with a standard diet displayed no degenerative changes.

The morphologically distinct reduction of the degenerative changes of the penile tissue due to daltroban, reproducibly ascertained in further investigations, show that this compound possesses an inhibiting action on the degenerative processes of the penile tissue. The results demonstrate a new activity quality of the compound.

In this way, on the basis of daltroban, it is clearly shown that TXA$_2$ receptor antagonists reduce the increase of degenerative changes of the penis.

The here-described new use of TXA$_2$ receptor antagonists can be indicated not only in the case of metabolically healthy but also in the case of metabolically diseased subjects, for example dyslipidaemic and diabetic patients, in the case of normotonic subjects and also of hypertonic patients, when the above-described degenerative processes occur. In particular, an additional treatment with daltroban is indicated in the case of medication with the known appearance of potency disturbance.

The documents identified above as describing especially preferred $TXA_2$ receptor antagonist compounds are hereby incorporated by reference for the teaching of such compounds therein.

While it is preferred to administer a single $TXA_2$ receptor antagonist to patients, it will be readily appreciated by those skilled in the art that mixtures of $TXA_2$ receptor antagonists can be used if desired.

We claim:

1. A method of preventing or reducing degenerative changes in penile tissue in a patient in need of such prevention or reduction, said method comprising administering to said patient an effective amount of at least one $TXA_2$ receptor antagonist.
2. The method of claim 1, wherein the degenerative change is atrophy of the corpus cavernosum.
3. The method of claim 1, wherein the degenerative change is cell nuclei degeneration.
4. The method of claim 1, wherein the degenerative change is the breakdown of myofilaments.
5. The method of claim 1, wherein a cause of the degenerative change is physical, chemical, surgical or pathological.
6. The method of claim 5, wherein the cause of the degenerative change is nicotine abuse or alcoholism.
7. The method of claim 1, wherein the $TXA_2$ receptor antagonist is daltroban.
8. The method of claim 7, wherein the daltroban is administered to the patient in a daily dosage of about 10 to about 1000 mg.
9. The method of claim 8, wherein the daily dosage is 100 to 800 mg.
10. The method of claim 8, wherein the daily dosage is administered in dosages units each containing 100 to 200 mg of daltroban.
11. The method according to claim 1, wherein said at least one $TXA_2$ receptor antagonist is administered orally.
12. The method of claim 1 for treating impotence.

* * * * *